US009381277B2

(12) United States Patent
Lehtonen et al.

(10) Patent No.: US 9,381,277 B2
(45) Date of Patent: Jul. 5, 2016

(54) RESORBABLE AND BIOCOMPATIBLE FIBRE GLASS COMPOSITIONS AND THEIR USES

(71) Applicant: Purac Biochem bv, AC Gorinchem (NL)

(72) Inventors: Timo Lehtonen, Lempaala (FI); Jukka Tuominen, Berkel en Rodenrijs (NL); Fredrik Ollila, Turku (FI)

(73) Assignee: Purac Biochem bv, AC Gorinchem (NL)

( * ) Notice: Subject to any disclaimer, the term of this patent is extended or adjusted under 35 U.S.C. 154(b) by 0 days.

(21) Appl. No.: 14/245,071

(22) Filed: Apr. 4, 2014

(65) Prior Publication Data

US 2014/0220338 A1 Aug. 7, 2014

Related U.S. Application Data

(63) Continuation of application No. 13/265,832, filed as application No. PCT/EP2010/055192 on Apr. 20, 2010, now abandoned.

(30) Foreign Application Priority Data

Apr. 23, 2009 (EP) ..................... 09158608

(51) Int. Cl.
| | |
|---|---|
| *C03C 3/04* | (2006.01) |
| *C03C 3/087* | (2006.01) |
| *C03C 3/095* | (2006.01) |
| *C03C 3/078* | (2006.01) |
| *A61K 8/25* | (2006.01) |
| *A61K 33/42* | (2006.01) |
| *A61K 33/08* | (2006.01) |
| *A61L 31/02* | (2006.01) |
| *A61L 27/10* | (2006.01) |
| *A61L 27/44* | (2006.01) |
| *A61L 27/58* | (2006.01) |
| *A61L 31/12* | (2006.01) |
| *A61L 31/14* | (2006.01) |
| *C03C 3/091* | (2006.01) |
| *C03C 3/097* | (2006.01) |
| *C03C 4/00* | (2006.01) |

(52) U.S. Cl.
CPC .............. *A61L 31/026* (2013.01); *A61L 27/10* (2013.01); *A61L 27/446* (2013.01); *A61L 27/58* (2013.01); *A61L 31/127* (2013.01); *A61L 31/128* (2013.01); *A61L 31/148* (2013.01); *C03C 3/078* (2013.01); *C03C 3/091* (2013.01); *C03C 3/097* (2013.01); *C03C 4/0007* (2013.01); *C03C 2201/10* (2013.01); *C03C 2201/28* (2013.01); *C03C 2213/02* (2013.01); *Y10T 428/29* (2015.01)

(58) Field of Classification Search
CPC ..... A61K 6/0273; A61K 33/42; A61K 33/00; A61K 6/0255; A61K 6/025; A61K 6/083; A61K 8/25; A61K 33/08; A61L 27/10; A61L 27/58; C03C 4/0007; C03C 10/0009
See application file for complete search history.

(56) References Cited

U.S. PATENT DOCUMENTS

| | | | |
|---|---|---|---|
| 5,108,957 A | 4/1992 | Cohen et al. | 501/35 |
| 5,645,934 A * | 7/1997 | Marcolongo et al. | 428/357 |
| 6,399,693 B1 | 6/2002 | Brennan et al. | 524/494 |
| 2005/0008620 A1 | 1/2005 | Shimp et al. | 424/93.7 |
| 2005/0142077 A1 | 6/2005 | Zimmer et al. | 424/57 |
| 2007/0278720 A1 | 12/2007 | Wang et al. | 264/430 |

FOREIGN PATENT DOCUMENTS

| | | |
|---|---|---|
| EP | 0 412 878 | 2/1991 |
| EP | 1 048 625 | 11/2000 |
| EP | 1 665 042 | 5/2006 |
| FR | 2 658 182 | 8/1991 |
| FR | 2 781 788 | 2/2002 |
| WO | WO 94/14401 | 7/1994 |
| WO | WO 96/21628 | 7/1996 |
| WO | WO 98/46164 | 10/1998 |

OTHER PUBLICATIONS

Kellomaki et al., "Bioabsorbable scaffolds for guided bone regeneration and generation," 21 *Biomaterials* 2495 (2000).
Clupper et al., "In Vitro Bioactivity of S520 Glass Fiber and Initial Assessment of Osteoblast Attachment," 67A *J. Biomed. Mater. Res.* 285 (2003).
Frantzén, "Bioactive Glass in Lumbar Spondylodesis, a Pre-Clinical and Clinical Study," Doctoral Thesis (University of Turku 2012).
"Cytotoxicity Assay In Vitro: Evaluation of Materials for Medical Devices (Colony Forming Ability) With FiberLive Composite" (Harlan Laboratories Ltd. 2011).

* cited by examiner

*Primary Examiner* — Frederick Krass
*Assistant Examiner* — Tracy Liu
(74) *Attorney, Agent, or Firm* — James C. Lydon

(57) ABSTRACT

Biocompatible and resorbable melt derived glass compositions which include: $SiO_2$ 60-70 weight-%, $Na_2O$ 5-20 weight-%, CaO 5-25 weight-%, MgO 0-10 weight-%, $P_2O_5$ 0.5-3.0 weight-%, $B_2O_3$ 0-15 weight-%, $Al_2O_3$ 0-5 weight-%, and which contain less than 0.05 weight-% potassium. Biocompatible and resorbable glass fibers manufactured from these glass compositions, medical devices containing fibers of the invention, the use of these compositions for the manufacture of glass fiber and the use of the fibers for the manufacture of medical devices are also disclosed.

14 Claims, 1 Drawing Sheet

RESORBABLE AND BIOCOMPATIBLE FIBRE GLASS COMPOSITIONS AND THEIR USES

FIELD OF INVENTION

The invention relates to potassium free melt derived resorbable and biocompatible glass compositions, fibre glass of such compositions and use thereof for the manufacture of medical devices, as well as to medical devices comprising such resorbable fibres.

BACKGROUND OF THE INVENTION

Various bioactive glass compositions are known in the field. They are able to bond to bone and soft tissue, and they may be used for stimulating tissue or bone growth in a mammalian body. Bioactive glass also typically guides the formation of new tissue, which grows within said glass. When bioactive glasses come into contact with a physiological environment, a layer of silica gel is formed on the surface of the glass. Following this reaction, calcium phosphate is deposited to this layer and finally crystallized to a hydroxyl-carbonate apatite. Due to this hydroxyl-carbonate apatite layer the resorption of the bioactive glasses is slowed down when inserted into mammalian bodies.

Other types of resorbable glass compositions are also known in the field. Resorbable glasses are not necessarily bioactive, i.e. they do not form a hydroxyl-carbonate apatite layer on the glass surface. Resorbable glass compositions are used in the glass fibre industry to resolve the problem of glass fibres ending up e.g. in lungs during installation of glass fibre insulation. Disappearance of the fibres is preferably relatively fast, so that no detrimental effects are caused to the body. One resorbable glass composition is disclosed in EP 0 412 878. The fibres are degraded within 32 days. Such a degradation rate is, however, too fast for most medical applications, for example for screws or pins for fixing bone defects or fractures.

EP 0 915 812 B1 and EP 1 484 292 A1 disclose biosoluble glass composition to improve occupational health and safety. WO 03/018496 A1 discloses anti-inflammatory, wound-healing glass powder compositions. U.S. Pat. No. 6,482,444 B1 discloses silver-containing bioactive sol-gel derived glass compositions to be used in implanted materials, for preparation of devices used for in vitro and ex vivo cell culture.

EP0802890B1 discloses a bioactive glass composition with a large working range. Devitrification problems are circumvented by adding potassium and optionally magnesium to the glass.

OBJECT AND SUMMARY OF THE INVENTION

An object of the present invention is to provide a biocompatible and resorbable melt derived glass composition.

Another object of the present invention is to provide biocompatible and resorbable glass fibre.

A further object of the present invention is to provide a medical device.

A still further object of the present invention is to provide use of and resorbable melt derived glass composition and fibre.

Thus the present invention provides a biocompatible and resorbable melt derived glass composition comprising:

| | |
|---|---|
| $SiO_2$ | 60-70 weight-%, |
| $Na_2O$ | 5-20 weight-%, |
| CaO | 5-25 weight-%, |
| MgO | 0-10 weight-%, |
| $P_2O_5$ | 0.5-3.0 weight-%, |

-continued

| | |
|---|---|
| $B_2O_3$ | 0-15 weight-%, |
| $Al_2O_3$ | 0-5 weight-% and |
| $Li_2O$ | 0-1 weight-%, |
| comprising less than 0.05 weight-% potassium. | |

The present invention also provides biocompatible and resorbable glass fibre manufactured from a biocompatible and resorbable melt derived glass composition of the invention.

The present invention further provides a medical device comprising fibre of the invention.

The present invention still further provides use of the biocompatible and resorbable melt derived glass composition of the invention for the manufacture of glass fibre and use of the fibres of the invention for the manufacture of a medical device.

DETAILED DESCRIPTION OF THE INVENTION

Definitions

Figure 1:
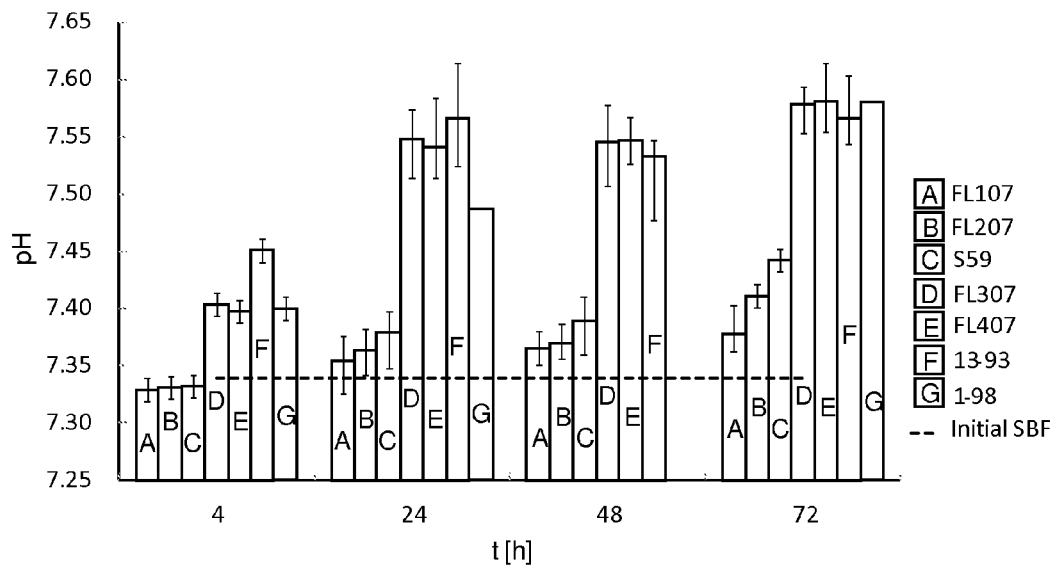
FIG. 1 illustrates pH change in SBF dissolution tests as a function of dissolution time of fibres of different fibre compositions including a composition according to the present invention.

The terms used in this application, if not otherwise defined, are those agreed on at the consensus conference on biomaterials in 1987 and 1992, see Williams, D F (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992.

In this application, by bioactive material is meant a material that has been designed to elicit or modulate biological activity. Bioactive material is often surface-active material that is able to chemically bond with the mammalian tissues.

The term resorbable in this context means that the material is disintegrated, i.e. decomposed, upon prolonged implantation when inserted into mammalian body and when it comes into contact with a physiological environment. Especially, the term resorbable glass means silica-rich glass that does not form a hydroxyl-carbonate apatite layer on its surface when in contact with a physiological environment. Resorbable glass disappears from the body through resorption and does not significantly activate cells or cell growth during its decomposition process.

By biomaterial is meant a material intended to interface with biological systems to evaluate, treat, augment or replace any tissue, organ or function of the body. By biocompatibility is meant the ability of a material used in a medical device to perform safely and adequately by causing an appropriate host response in a specific location. By resorption is meant decomposition of biomaterial because of simple dissolution. By composite is meant a material comprising at least two different constituents, for example an organic polymer and a ceramic material, such as glass.

By melt derived glass fibre is meant glass fibre manufactured by melting glass in a crucible at 700-1500° C. and pulling glass fibres of the molten glass through holes of the crucible, resulting in fibres with a diameter in the range of 5-300 µm (micrometers).

In the present context the term medical devices relates to any kind of implant used within the body, as well as devices used for supporting tissue or bone healing or regeneration. An implant according to the present context comprises any kind of implant used for surgical musculoskeletal applications such as screws, plates, pins, tacks or nails for the fixation of bone fractures and/or osteotomies to immobilise the bone fragments for healing; suture anchors, tacks, screws, bolts, nails, clamps, stents and other devices for soft tissue-to-bone, soft tissue—into-bone and soft tissue-to-soft tissue fixation; as well as devices used for supporting tissue or bone healing or regeneration; or cervical wedges and lumbar cages and plates and screws for postero-lateral vertebral fusion, interbody fusion and other operations in spinal surgery. Depending on the application and purpose of the medical device material, the medical devices are expected and designed to be biocompatible and exhibit controlled resorption in the mammalian body. The optimal resorption rate is directly proportional to the renewal rate of the tissue in the desired implantation location. In the case of bone tissue, a considerable proportion of the implant is preferably resorbed/decomposed within 6 to 14 weeks depending on the application, in the tissue. In cases where physical support to the healing tissues is desirable the resorption rate might be several months or even several years. Furthermore, the invention can be made use of in medical devices such as canules, catheters and stents. The invention can be made use of in fibre reinforced scaffolds for tissue engineering.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

Preferred Embodiments of the Invention

The present invention provides a slowly resorbable and biocompatible fibre glass composition suitable for use in medical devices. Resorption of degradable glasses is a function of composition and surface to volume ratio i.e. surface erosion by physiological environment. Due to high surface to volume ratio of fibres, release of alkali and alkali earth metal ions to a physiological environment can be undesirably fast. Thus it is important to know and to be able to control the resorption rate of glass and release of alkali and alkali earth metal ions to a physiological environment. Bioactive fibre glasses start to react immediately when contacted with aqueous solutions by alkali exchange reactions, i.e. sodium and potassium ions in the glass are replaced by hydrogen ions from the solution. A rapid and high degree of dissolution will locally increase the pH of surrounding interstitial fluid, in spite of its buffering capacity, to undesirably high values. Further, body fluids contain a relatively high content of sodium but a low content of potassium ions. Thus, rapid leaching of potassium ions from glasses is likely to have a much higher relative influence on the local body fluid composition than leaching of sodium ions, i.e. alkali metal ions are responsible for a high local detrimental pH increase and also in certain cases potassium may cause physiological problems through neurotoxic and cytotoxic effects Now it has been surprisingly found out that omitting potassium from the melt derived glass fibre compositions will increase biocompatibility and eliminate neurotoxic and cytotoxic effects. Potassium plays an important role in muscle contraction and nerve transmission. Muscle and nerve cells have specialized channels for moving potassium in and out of the cell. It is well known in the art that when increased amounts of potassium is in the extracellular matrix in tissues the cells of, e.g. muscles and nerves can be damaged, i.e. can be toxic to human tissues.

Furthermore, by varying the amount of silica and other components i.e. $Na_2O$, $CaO$, $MgO$, $P_2O_5$, $B_2O_3$, and $Al_2O_3$ in the glass composition presented in this invention, the resorption rate of the glass fibres can be easily controlled and tailor-made for diverging end applications.

According to one aspect of the present invention the amounts of $SiO_2$ and $Na_2O$ are important features and should be kept at quantities preferably between 60 and 70 weight-% and between 5 and 20 weight-% respectively to sustain resorbability of the glass fibre without giving rise to high amounts of released alkali metals thus preventing a detrimental or toxicological local pH peak in a physiological environment. In addition, in order to retain long term bioactivity i.e. CaP formation of the glass, fibres phosphorous and calcium oxides are required in sufficient amounts. Moreover, aluminium and boric oxide can be used to reduce solubility, and magnesium oxide can be added to increase elasticity and enhance the fibre formation from melt.

A typical potassium free, i.e. comprising at most only minute amounts of potassium, resorbable melt derived glass composition suitable for the present invention comprises

| | |
|---|---|
| $SiO_2$ | 60-70 weight-%, |
| $Na_2O$ | 5-20 weight-%, |
| $CaO$ | 5-25 weight-%, |
| $MgO$ | 0-10 weight-%, |
| $P_2O_5$ | 0.5-3.0 weight-%, |
| $B_2O_3$ | 0-15 weight-%, |
| $Al_2O_3$ | 0-5 weight-% and |
| $Li_2O$ | 0-1 weight-% |

Although the glass composition is potassium free, it may include potassium, e.g. as an impurity from raw materials, but not more than 0.05 weight-%, preferably not more than 0.03 weight-%, more preferably not more than 0.01 weight-% and most preferably not more than 0.005 weight-%. Potassium is preferably excluded and should be avoided even as an impurity.

Many preferred compositions of the invention comprise

| | |
|---|---|
| $SiO_2$ | 62-68 weight-%, |
| $Na_2O$ | 10-15 weight-%, |
| $CaO$ | 8-20 weight-%, |
| $MgO$ | 0-10 weight-%, |
| $P_2O_5$ | 0.5-3 weight-%, |
| $B_2O_3$ | 0-4 weight-% and |
| $Al_2O_3$ | 0-2.5 weight. |

Many other preferred compositions of the invention comprise

| | |
|---|---|
| $SiO_2$ | 62-68 weight-%, |
| $Na_2O$ | 10-15 weight-%, |
| $CaO$ | 10-20 weight-%, |
| $MgO$ | 0-10 weight-%, |
| $P_2O_5$ | 0.5-3 weight-%, |
| $B_2O_3$ | 1.3-4 weight-% and |
| $Al_2O_3$ | 0-2.5 weight |

Some preferred compositions of the invention comprise

| | |
|---|---|
| $SiO_2$ | 62-68 weight-%, |
| $Na_2O$ | 10-15 weight-%, |
| CaO | 8-20 weight-%, |
| MgO | 0-6 weight-%, |
| $P_2O_5$ | 0.5-3 weight-%, |
| $B_2O_3$ | 0-4 weight-% and |
| $Al_2O_3$ | 0-2.5 weight. |

Some other preferred compositions of the invention comprise

| | |
|---|---|
| $SiO_2$ | 64-66 weight-%, |
| $Na_2O$ | 5-10 weight-%, |
| CaO | 11-18 weight-%, |
| MgO | 2-8 weight-%, |
| $P_2O_5$ | 0.5-3 weight-%, |
| $B_2O_3$ | 0-5 weight-% and |
| $Al_2O_3$ | 0-1.0 weight. |

Some further preferred compositions of the invention comprise

| | |
|---|---|
| $SiO_2$ | 64-66 weight-%, |
| $Na_2O$ | 5-10 weight-%, |
| CaO | 12-18 weight-%, |
| MgO | 2-6 weight-%, |
| $P_2O_5$ | 0.5-3 weight-%, |
| $B_2O_3$ | 0-3 weight-%, and |
| $Al_2O_3$ | 0-1.0 weight-%. |

Resorbable and biocompatible melt derived glass fibres of the present invention are manufactured from resorbable glass compositions according to the invention. Preferred fibres according to the invention are manufactured from preferred compositions of the invention.

The time for typical fibres of the invention to be fully resorbed in vitro in simulated body fluid (SBF), calculated using a resorption rate determined by dissolution in sink at +37° C. using the linear portion of the resorption curve, is 1-100, preferably 2-45, more preferably 3-15, even more preferably 4-70, still more preferably 5-30 and most preferably 6-15 months.

The thickness of typical fibres of the invention is <300 µm, preferably 1-75 µm, more preferably 5-30 µm, even more preferably 10-25 µm, still more preferably 10-20 µm and most preferably about 15 µm.

The tensile strength of typical fibres of the invention is 0.7-3 GPa, preferably 0.9-2.5 GPa, more preferably 1.0-2.0 GPa and most more preferably 1.5-2.0 GPa.

The tensile strength of other typical fibres of the invention is 0.6-2 GPa, preferably 0.9-1.8 GPa, more preferably 1.0-1.6 GPa and most more preferably 1.1-1.5 GPa.

Medical devices according to the invention comprise fibres of the invention. Preferred medical devices according to the present invention comprise preferred fibres of the invention.

Many preferred devices according to the invention are fully based on or comprise chopped and/or continuous fibre of the invention; and/or any kind of textile, woven or non-woven comprising fibre according of the invention.

Typical medical devices of the invention are any kind of implants used within the body, preferably selected from the group consisting of a joint implant, an internal/external fixation device, a stent a, pin, a nail, a screw, a spike, a stud, a plate, and a device for supporting tissue or bone healing and/or regeneration.

In some preferred embodiments of medical devices of the invention the amount of fibre according to the invention is >10 volume-%, preferably >40 volume-%, more preferably >60 volume-%, most preferably >90 volume-% of the total volume of the fibres of said medical device.

In some preferred embodiments of the invention the fibres are embedded in a continuous polymer matrix. Preferably the polymer matrix comprises at least one polymer selected from the group consisting of polyglycolide (PGA); copolymers of glycolide, such as glycolide/L-lactide copolymers (PGA/PLLA), glycolide/trimethylene carbonate copolymers (PGA/TMC); polylactides (PLA); stereocopolymers of PLA, such as poly-L-lactide (PLLA), poly-DL-lactide (PDLLA), L-lactide/DL-lactide copolymers; other copolymers of PLA, such as lactide/tetramethylglycolide copolymers, lactide/trimethylene carbonate copolymers, lactide/d-valerolactone copolymers, lactidek-caprolactone copolymers; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically 3,6-substituted poly-1,4-dioxane-2,5-diones; polyhydroxyalkanoates, such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone; poly-ε-caprolactone; methyl-methacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA); poly-b-alkanoic acids; polycarbonates; polyorthoesters; polyphosphates; poly(ester anhydrides) and mixtures or thermosets thereof; and preferably selected from the group consisting of poly(ε-caprolactone), poly(ε-caprolactone-1-lactide) copolymers, polylactide-co-glycolide and polylactide.

Fibres as such or comprised in the medical devices are resorbable and biocompatible when exposed to a physiological environment.

The above mentioned glass compositions are manufactured according to a standard melt processes known in the art, except for a certain limitation that is included in the fibre glass manufacturing process. Special focus is required on raw material purity, particle size distribution, homogeneity derived from the sequence of melting, crushing and re-melting process. A homogeneous glass preform, manufactured by the melt process, is then drawn to fibre according to process described in patent application EP1958925A1. Because resorbable and bioactive glasses have a strong tendency to transfer from the amorphous glass state to the crystalline state when heating glass proprietary technology, e.g. technology disclosed in patent application EP1958925A1 enabling the manufacture of a wide range of resorbable and bioactive glasses circumventing problems relating to crystallization during fibre production, to produce fibres is preferably used.

It is known for the persons skilled in the art that most biodegradable glass compositions are unsuitable for melt derived fibre drawing due to crystallization properties, melt viscosity properties and melt strength. It has been surprisingly discovered in this invention that the above mentioned compositions are feasible for fibre drawing also in industrial scale with the method described in patent application EP1958925A1 even though the composition lacks the fibre drawing facilitating (and cytotoxic) component $K_2O$. The fibres show improved strength properties, when compared for example to polymer fibres having the same diameter. According to one embodiment of the invention, suitable glass fibres normally show a tensile strength of 700 MPa-3 GPa, more typically 900 MPa-2.5 GPa, preferably 1.0-2.0 GPa, more preferably 1.5-2.0 GPa. Comparable polymer fibres have typically a tensile strength of 300-600 MPa. Modulus for glass fibres is typically 50-100 GPa, more typically 60-80 GPa, preferably 65-75 GPa.

The advantage of the medical devices according to the present invention is that they disappear from the body by degradation without giving rise to toxic effects through the release of potassium and/or a high local pH.

Another advantage of the medical devices according to the invention is their strength and feasibility of manufacture. A medical device according to the present invention can be manufactured by arranging the fibres with a polymer matrix, preferably with a resorbable polymer matrix, and using any type of polymer processing equipment, e.g. open or closed batch mixer or kneader, continuous stirring tank reactor or mixer, extruder, injection moulding machine, RIM, tube reactor or other standard melt processing or melt mixing equipment known in the field, producing and/or shaping the arranged fibres with the polymer matrix into an implant having a desired orientation of the continuous fibres and/or chopped/cut fibres and/or woven, non-woven mats/textiles. One advantage of the present invention is that the melting temperature of the matrix material is around 30-300° C., and the glass transition temperature of the fibres around 450-650° C. Consequently, the glass fibres are not damaged by the temperature of the melted matrix material and a strong fibre reinforced medical device is obtained when the matrix is let to solidify. The implants according to the present invention can also be manufactured by using any type of polymer processing equipment, e.g. open or closed batch mixer or kneader, continuous stirring tank reactor or mixer, extruder, injection molding machine, RIM, tube reactor, or other standard melt processing or melt mixing equipment known in the field.

The glass composition according to the present invention is, in addition to being resorbable, also biocompatible. It can thus be implanted in mammals, such as humans, and it does not react in an undesirable manner, cause any side effects or reject the surrounding tissues.

The resorption rate of the resorbable glass composition according to the present invention is normally 1-100, 3-30, 4-80, 5-45, 6-20, sometimes 8-16 months, which resorption rates are sufficient for medical applications. For example, a typical resorption rate for an anterior cruciate ligament screw is 3-24 months, the silica content of the composition then being approximately from 60 to 65 weight-%. The typical resorption rate is 12-24 months when the composition is used for medical devices suitable for internal fixation devices, the silica content of the composition then being approximately from 66 to 70 weight-%.

The resorption rate or degradation can be measured by measuring the silica ion concentration dissolved at certain immersion times in aqueous solution. A method suitable for measuring resorption rates, i.e. glass fibre disintegration, is disclosed for example in J. Korventausta et al., Biomaterials, Vol. 24, Issue 28, December 2003, pp. 5173-5182. Another way to measure degradation is to monitor weight loss, pH change and mechanical strength loss in aqueous solution.

The present invention also relates to resorbable and biocompatible glass fibres manufactured from resorbable and biocompatible glass compositions as defined above. All the features and embodiments listed above in connection with the suitable resorbable and biocompatible glass compositions apply mutatis mutandis to the suitable fibres and to the medical devices according to the present invention.

According to one embodiment of the invention the thickness of the fibres suitable for the present invention is <300 µm, typically 1-75 µm, more typically 5-30 µm, preferably 10-25 µm, more preferably 10-20 µm, usually approximately 15 µm. The fibres can be used as long single fibres, as yarns, braids, rovings, and bands or as different types of fabrics made by using the methods of textile technology.

The fibres can also be used as chopped fibres and mats or textiles manufactured from chopped fibre. For example, according to one embodiment of the invention fibres having a diameter <300 µm, typically 1-75 µm, more typically 5-30 µm, preferably 10-25 µm, more preferably 10-20 µm, usually approximately 15 µm can be used as chopped fibres. Chopped fibres can be used also for preparing non-woven textile-like materials. These non-woven textiles can be combined with resorbable plastics and can be used for example for the manufacture of hot moulded implants. Chopped fibres can also be used to reinforce implants that are manufactured by injection moulding or other processing techniques known in the field of polymer processing.

According to one embodiment of the invention the length of the chopped fibres is <20 mm, typically 0.5-10 mm, more typically 1-5 mm, preferably 3-5 mm, usually approximately 5 mm. According to another embodiment of the invention the length of the continuous fibres is >20 mm, preferably >30 mm, usually more than 40 mm or most preferably as fully continuous fibre in pultrusion as an example.

The resorbable glass composition suitable for the present invention can be used for manufacturing various medical devices. Such devices can be used to support and strengthen the defect site during healing, and can form part of the tissue once the defect is healed. Due to the long term bioactivity of some of the compositions mentioned above the tissue may grow within the resorbable material and function as a tissue regenerating scaffold.

The medical device according to the present invention comprises a polymer matrix, preferably a continuous polymer matrix, but not excluding discontinuous polymer matrix, which polymer matrix is naturally biocompatible. Said biocompatible polymer matrix may be and preferably is also resorbable, however not excluding biostable biocompatible polymers.

The resorbable glass fibres are preferably embedded in a continuous polymer matrix, which means that the surfaces of the fibres are covered by said polymer. Preferably, at least 80% of the surfaces of the fibres are covered by the polymer matrix, more preferably at least 90%, and most preferably at least 95% of the surface of the fibres is covered by the polymer matrix. Preferably also at least 99% of the fibres of the surface of the medical device are covered by the polymer matrix.

According to the present invention the fibres can be used as load bearing component embedded a degradable matrix in a tissue engineering medical device with or without higher bioactivity and resorption rate containing degradable glass, which can be in form of granules, spheres, blocks and fibres.

According to the present invention the fibres can be used as a bioactive component embedded in a degradable matrix in a porous tissue engineering scaffold. Preferably, the scaffold has a porosity degree of 60%, more preferably at least 80%, and most preferably at least 90%.

The polymer matrix material of the medical device according to the present invention may be selected from the group consisting of biocompatible polymers, such as polymers of methacrylic acid, acrylic acid and vinylpyrrolidone, polyolefins, polyalkylene oxides, polyvinylalcohol, polylactones, polycarbonates, poly-anhydrides, aliphatic polyesters, polyamides, polyimides, liquid crystal polymers, polyorthoesters, copolymers of the above mentioned and thermosets of above mentioned polymers, polymers and copolymers based on units derived from hydroxyacids and natural polymers, such as sugars, starch, cellulose and cellulose derivatives, polysaccharides, collagen, chitosan, fibrin, hyalyronic acid, polypeptides and proteins.

The polymer matrix material may thus be either a biostable or a resorbable material. The material can be porous or it can become porous during the use and/or when in contact with the tissue. Biostable polymers do not dissolve or react in contact with body fluids or tissue. Some suitable biostable polymers are derivatives of acrylic acid or methacrylic acid, such as methyl(methacrylate). Some suitable resorbable polymers are homo- and copolymers of lactones and lactides and polycarbonates. The polymer may be a biodegradable and/or bioresorbable polymer and/or a biopolymer, preferably derived from hydroxyl acid units, a preferred polymeric material being poly($\epsilon$-caprolactone-1-lactide) copolymer or poly($\epsilon$-caprolactone) or poly(dl-lactide) or poly(l-lactide) or poly(l-lactide-co-glycolide). Mixtures of any of the above-mentioned polymers and their various forms may also be used. For some embodiments also gutta-percha may be used.

According to one embodiment of the invention also following resorbable polymers, copolymers and terpolymers may be used as matrix material: polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactidek-caprolactone copolymers; terpolymers of PLA, such as lactide/glycolide/trimethylene carbonate terpolymers, lactide/glycolidek-caprolactone terpolymers, PLA/polyethylene oxide copolymers; polydepsipeptides; unsymmetrically 3,6-substituted poly-1,4-dioxane-2,5-diones; polyhydroxyalkanoates, such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-$\epsilon$-caprolactone; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA); poly-b-alkanoic acids; polycarbonates; polyorthoesters; polyphosphates; poly(ester anhydrides); and mixtures thereof; and thermosets of above mentioned polymers.

The medical device according to the present invention may also comprise bioactive glass fibres, such as fibres made of compositions disclosed in EP 080 2890 and EP 1405 647. The medical device may also comprise polymer fibres, such as fibres of any of the polymers mentioned above in connection with the polymer matrix. However, the amount of resorbable glass fibres is usually >10 volume-%, preferably >40 volume-%, more preferably >60 volume-%, most preferably >90 volume-% of the total volume of the fibres of the medical device.

According to still another embodiment of the present invention the medical device may comprise two or more types of resorbable fibres, each type having a different composition. The medical device may also comprise two or more groups of fibres having different median diameter. It is also possible that all of the fibres of the medical device do not have the same diameter, but the diameter may vary as desired.

All the fibres used in the medical devices according to the present invention may be in various forms such as continuous fibres or chopped fibres. Their orientation can also be freely chosen depending on the medical device in which they are used and in function of the intended use.

EXAMPLES

Embodiments of the present invention will now be described in more detail in the following examples. The examples are illustrative but not limiting the compositions, methods and applications of the present invention, which are obvious to those skilled in the art.

General manufacture of a biodegradable glass preform was made according to the following procedure: dry-mix of raw materials, melting in pt-crucible in furnace, annealing, crushing, re-melting and annealing from following raw material sources: $SiO_2$, $Al_2O_3$, $Na_2CO_3$, $(CaHPO_4)(H_2O)$, $CaCO_3$, $H_3BO_3$ and MgO. Fibre drawing was conducted according to method in patent application EP1958925A1.

Example 1

Glass Fibre Compositions Manufactured for a pH Study

According to the general procedure the following compositions were used for preform and fibre manufacturing for a pH study:

| Glass code | $Na_2O$ | $K_2O$ | MgO | CaO | $B_2O_3$ | $P_2O_5$ | $SiO_2$ | Resorption rate |
|---|---|---|---|---|---|---|---|---|
| FL107 | 10 | 0 | 6 | 16 | 2 | 2 | 64 | Slow |
| FL207 | 5 | 5 | 6 | 16 | 2 | 2 | 64 | Slow |
| FL307 | 5 | 10 | 3 | 22 | 2 | 2 | 56 | Fast |
| FL407 | 10 | 5 | 3 | 22 | 2 | 2 | 56 | Fast |
| S59 | 25.5 | 0 | 0 | 11 | 1.3 | 2.5 | 59.7 | Medium-fast |
| 13-93 | 6 | 12 | 5 | 20 | 0 | 4 | 53 | Fast |
| 1-98 | 6 | 11 | 5 | 22 | 1 | 2 | 53 | Fast |

The average fibre diameter was deducted to 35 μm by SEM images of fibre cross sections. Cut (16 mg) fibres were immersed in 16 ml simulated body fluid [SBF by Kokubo et. al. J. Biomed. Mater. Res. 24 (1990), p. 72], i.e. under in sink conditions. These values gave roughly the surface area to the volume of SBF ratio 0.4 $cm^{-1}$. The immersion time intervals used were between 4 and 72 hours. The samples were kept in a water bath at 37° C. After separating the samples from the SBF, the final pH of the solution was measured and the pH change during first 72 h is shown in FIG. 1.

The pH increase for the slowly reacting glass fibres FL107, FL207, and medium-fast S59, was minimal during the first four hours. No clear increase in pH can be deduced from the results. In contrast, the pH of the other glasses had increased already during this time interval. The pH increased linearly for the slow glasses during the first 72 h, while the pH of the fast glasses increased more rapidly during first 24 h, after which the pH increase rate slowed down. This suggests that a reaction layer formation of calcium phosphates started for the fast glasses already after 24 h thereby forming a diffusion barrier between the solution and glass. The pH continued to increase linearly for the slow glasses up to one week after which the rate decreased. The decreased rate suggests that the CaP layer formation has initiated, and thus acted as a protective layer against leaching.

Example 2

In vitro Testing of a Fast Resorption Rate Potassium Containing Fibre Glass Composition 1-98 with Stem Cells A fast resorbable potassium containing fibre glass composition 1-98, presented above in example 1, was tested in vitro with human adipose stem cells cultured in DMEM-F12 supplemented with 10% foetal bovine serum (FBS), 1% antibiotic/antimocotic and 1% L-glutamine at 37° C. in a humidified 5% $CO_2$ atmosphere. Before combining fibre glass 1-98 and cells, the fibre glass was first washed three times with the cell growth medium and then incubated with cell growth medium for 48 hours. Cell viability was tested using a non-quantitative dead/alive staining method.

The result of cell viability testing was the following:
a notable and rapid increase of cell growth medium pH
almost all the cells died when cultured for three days on 1-98 fibre glass
few living cells that were growing on the fibre surface had abnormal morphology, indicated by green cytoplasmic staining Example 3

Slow Resorbable and Biocompatible Fibre Glass with Aluminium and Low Phosphorous Content
According to the general procedure the following composition was used for preform and fibre manufacturing:

| | |
|---|---|
| $SiO_2$ | 64.0 weight-%, |
| $Na_2O$ | 11.0 weight-%, |
| CaO | 18.0 weight-%, |
| $B_2O_3$ | 2.0 weight-% |
| MgO | 2.0 weight-% |
| $P_2O_5$ | 0.5 weight-%, |
| $Al_2O_3$ | 2.5 weight-%, |

After drawing the fibres were stored in foil bags under protective gas and stored for further analyses and use. The composition and amorphous nature was confirmed using XRF and XRD, respectively. The average fibre diameter was around 35 μm.

Example 4

Slow Resorbable and Biocompatible Fibre Glass with High Silicon Content
According to the general procedure the following composition was used for preform and fibre manufacturing:

| | |
|---|---|
| $SiO_2$ | 65.5 weight-%, |
| $Na_2O$ | 12.0 weight-%, |
| CaO | 18.0 weight-%, |
| $P_2O_5$ | 1.5 weight-%, |
| $B_2O_3$ | 2.0 weight-%, |
| MgO | 1.0 weight-% |

After drawing the fibres were stored in foil bags under protective gas and stored for further analyses and use. The composition and amorphous nature was confirmed using XRF and XRD, respectively. The average fibre diameter was around 35 μm.

Example 5

Slow Resorbable and Biocompatible Fibre Glass with High Sodium and Magnesium Content
According to the general procedure the following composition was used for preform and fibre manufacturing:

| | |
|---|---|
| $SiO_2$ | 64.0 weight-%, |
| $Na_2O$ | 16.0 weight-%, |
| CaO | 14.0 weight-%, |
| $P_2O_5$ | 1.0 weight-%, |
| $B_2O_3$ | 1.5 weight-%, |
| MgO | 3.5 weight-% |

After drawing the fibres were stored in foil bags under protective gas and stored for further analyses and use. The composition and amorphous nature was confirmed using XRF and XRD, respectively. The average fibre diameter was around 35 μm.

Example 6

Slow Resorbable and Biocompatible Fibre Glass with Low Sodium and High Calcium Content
According to the general procedure the following composition was used for preform and fibre manufacturing:

| | |
|---|---|
| $SiO_2$ | 61.0 weight-%, |
| $Na_2O$ | 10.0 weight-%, |
| CaO | 22.0 weight-%, |
| $P_2O_5$ | 3.0 weight-%, |
| $B_2O_3$ | 1.0 weight-%, |
| MgO | 3.0 weight-% |

After drawing the fibres were stored in foil bags under protective gas and stored for further analyses and use. The composition and amorphous nature was confirmed using XRF and XRD, respectively. The average fibre diameter was around 35 μm Example 7

Slow Resorbable and Biocompatible Fibre Glass Composition with Low Calcium and High Silicon Content
According to the general procedure the following composition was manufactured for preform and fibre manufacturing:

| Glass code | $Na_2O$ | $K_2O$ | MgO | CaO | $B_2O_3$ | $P_2O_5$ | $SiO_2$ | $Al_2O_3$ |
|---|---|---|---|---|---|---|---|---|
| NX-3 | 11.8 | 0 | 6.0 | 8.0 | 2.7 | 1.5 | 70.0 | 0 |
| NX-4 | 12.0 | 0 | 3.1 | 12.0 | 1.1 | 1.5 | 69.8 | 0.5 |
| NX-8 | 14.0 | 0 | 5.4 | 9.0 | 2.3 | 1.5 | 67.8 | 0 |
| NX-12 | 17.5 | 0 | 2.0 | 10.0 | 0 | 0.5 | 70.0 | 0 |

Example 8

Physical Properties of Glass Melt of Selected Resorbable and Biocompatible Potassium Free Glass Fibre Compositions
Physical properties (i.e. melt viscosity) was measured with high temperature rotational viscometer for selected resorbable and biocompatible potassium free glass fibre compositions:

| Glass code | $Na_2O$ | $K_2O$ | MgO | CaO | $B_2O_3$ | $P_2O_5$ | $SiO_2$ | $Al_2O_3$ |
|---|---|---|---|---|---|---|---|---|
| NC-02 | 11.0 | 0 | 2.0 | 18.0 | 2.0 | 0.5 | 64.0 | 2.5 |
| NC-021 | 11.0 | 0 | 2.0 | 18.0 | 2.0 | 0 | 64.5 | 2.5 |

| | Viscosity [dPas] | | | | |
|---|---|---|---|---|---|
| | 1.5 | 2 | 2.5 | 3 | 3.5 |
| Temp NC-02 [° C.] | 1470 | 1323 | 1207 | 1113 | 1035 |
| Temp NC-021 [° C.] | 1443 | 1320 | 1203 | 1112 | 1037 |

Example 9

Comparison of Tensile Properties of Selected Resorbable and Biocompatible Potassium Free Glass Fibres Against Commercial E-glass Comparison of the single glass fibre tensile behaviour, Favigraph semi-automatic fibre tensile tester equipped with 1N load cell was used, according to DIN EN ISO5079 and DIN 53835-2. The tensile test was conducted with gauge length of 50 mm and a cross head speed of 0.2 mm/min. Comparison was conducted between resorbable and biocompatible potassium free glass fibres against commercial E-glass fibre manufactured with same method and results presented as mean value from 50 parallel samples.

| Glass code | Na$_2$O | K$_2$O | MgO | CaO | B$_2$O$_3$ | P$_2$O$_5$ | SiO$_2$ | Al$_2$O$_3$ |
|---|---|---|---|---|---|---|---|---|
| NC-02 | 11.0 | 0 | 2.0 | 18.0 | 2.0 | 0.5 | 64.0 | 2.5 |
| NC-021 | 11.0 | 0 | 2.0 | 18.0 | 2.0 | 0 | 64.5 | 2.5 |

| Glass code | Diameter [μ] | Tensile Test [MPa] | Young's modulus [GPa] | Strain [%] |
|---|---|---|---|---|
| NC-02 | 13.9 | 2064 | 79.39 | 2.8 |
| NC-021 | 14.5 | 990 | 74.34 | 1.4 |
| E-glass | 15.6 | 1069 | 72.43 | 1.5 |

Example 10

Resorption of Glass Fibres as a Function of Mechanical Strength by Dissolution in Simulated Body Fluid (SBF)

According to general procedure following compositions were used for preform and fibre manufacturing:

| Glass code | Na$_2$O | K$_2$O | MgO | CaO | B$_2$O$_3$ | P$_2$O$_5$ | SiO$_2$ | Al$_2$O$_3$ |
|---|---|---|---|---|---|---|---|---|
| S59 | 25.5 | 0 | 0 | 11.0 | 1.3 | 2.5 | 59.7 | 0 |
| NC-02 | 11.0 | 0 | 2.0 | 18.0 | 2.0 | 0.5 | 64.0 | 2.5 |
| NC-06 | 12.0 | 0 | 1.0 | 18.0 | 2.0 | 1.5 | 65.5 | 0 |
| NC-07 | 16.0 | 0 | 3.5 | 14.0 | 1.5 | 1.0 | 64.0 | 0 |
| NC-09 | 10.0 | 0 | 3.0 | 22.0 | 1.0 | 3.0 | 61.0 | 0 |
| NC-10 | 10.0 | 0 | 6.0 | 16.0 | 1.0 | 3.0 | 64.0 | 0 |

Resorption of glass fibres were measured by loss of mechanical strength in SBF dissolution. Dissolution study was performed by immersing the fibres to SBF and the samples were withdrawn from after 0, 7 and 14 days and analysed. The tensile testing of fibres was done according to the ASTM C 1557-03 standard. The tensile strength is calculated from the ratio of the peak force and the cross-sectional area of the fibre.

Figure 2:
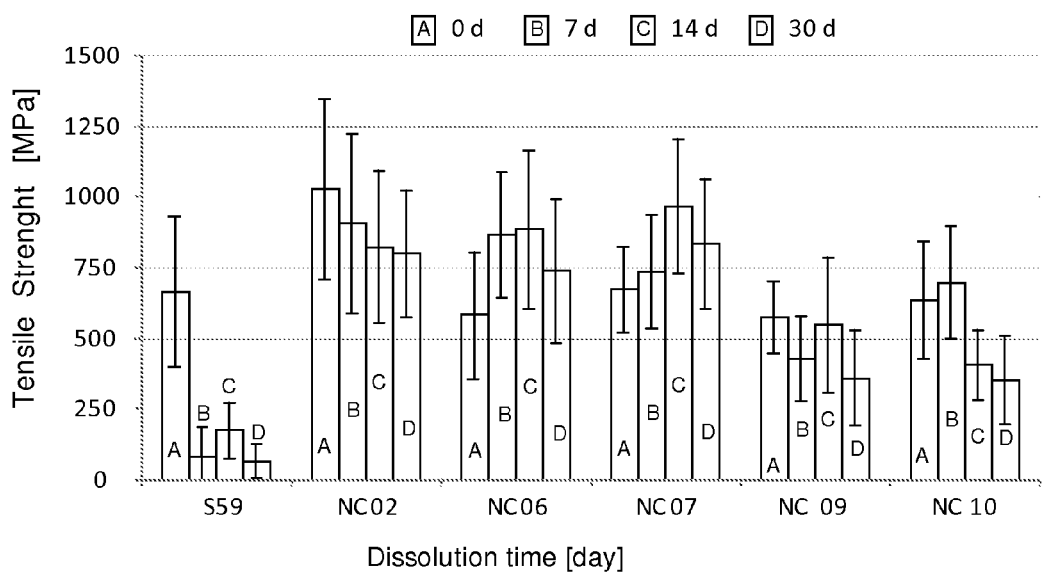
FIG. 2 illustrates the change of tensile strength in SBF dissolution tests as a function of dissolution time of different fibre compositions of the present invention.

Tensile strength results as a function of dissolution time are presented in FIG. 2. The results show that fast degradable fibre glass composition S59 lost its strength rapidly already after 7 days immersion time in SBF compared to glass fibre compositions according to the present invention.

Other Preferred Embodiments

It will be appreciated that the compositions, fibres, medical devices and uses of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. An implant comprising a biocompatible and resorbable glass fibre manufactured from a biocompatible and resorbable melt derived glass composition comprising:

| SiO$_2$ | 60-70 weight-%, |
|---|---|
| Na$_2$O | 5-20 weight-%, |
| CaO | 5-25 weight-%, |
| MgO | 0-10 weight-%, |
| P$_2$O$_5$ | 0.5-3.0 weight-%, |
| B$_2$O$_3$ | 0-15 weight-%, |
| Al$_2$O$_3$ | 0-5 weight-% and | comprising less than 0.05 weight-% potassium, said resorbable glass fiber having a full resorption time in vitro of 3-100 months when calculated using a resorption rate determined by dissolution in simulated body fluid under in sink conditions at +37° C. using a linear portion of a resorption curve.

2. The implant according to claim 1, wherein said glass fiber comprises chopped and/or continuous glass fibre.

3. The implant according to claim 1 wherein said implant is selected from the group consisting of a joint implant, an internal/external fixation device, a stent, a pin, a nail, a screw, a spike, a stud, a plate, and a device for supporting tissue or bone healing and/or regeneration.

4. The implant according to claim 1, wherein the amount of biocompatible and resorbable glass fibre is >10 volume-% of the total volume of the fibers of said implant.

5. The implant according to claim 1 wherein the fibers are embedded in a continuous polymer matrix.

6. The implant according to claim 5 wherein the polymer matrix comprises at least one polymer selected from the group consisting of polyglycolide (PGA); copolymers of glycolide; polylactides (PLA); stereocopolymers of PLA; copolymers of PLA; terpolymers of PLA; polydepsipeptides; unsymmetrically 3,6-substituted poly-1,4-dioxane-2,5-diones; polyhydroxyalkanoates; PHB/b-hydroxyvalerate copolymers (PHB/PHV); poly-b-hydroxypropionate (PHPA); poly-p-dioxanone (PDS); poly-d-valerolactone; poly-ϵ-caprolactone; methylmethacrylate-N-vinyl pyrrolidone copolymers; polyesteramides; polyesters of oxalic acid; polydihydropyrans; polyalkyl-2-cyanoacrylates; polyurethanes (PU); polyvinyl-alcohol (PVA); polypeptides; poly-b-malic acid (PMLA); poly-b-alkanoic acids; polycarbonates; polyorthoesters; polyphosphates; poly(ester anhydrides) and mixtures or thermosets thereof.

7. The implant according to claim 1 wherein said melt derived glass composition comprises less than 0.03 weight-% potassium.

8. The implant according to claim 1 wherein said melt derived glass composition comprises

| SiO$_2$ | 62-68 weight-%, |
|---|---|
| Na$_2$O | 10-15 weight-%, |
| CaO | 8-20 weight-%, |
| MgO | 0-10 weight-%, |
| P$_2$O$_5$ | 0.5-3 weight-%, |
| B$_2$O$_3$ | 0-4 weight-% and |
| Al$_2$O$_3$ | 0-2.5 weight-%. |

9. The implant of claim 1 wherein the thickness of the fibre is <300 μm.

10. The implant of claim 1 wherein the tensile strength of the fibre is 0.7-3 GPa.

11. The implant according to claim 6 wherein the stereo-copolymers of PLA are selected from the group consisting of poly-L-lactide (PLLA), poly-DL-lactide (PDLLA) and L-lactide/DL-lactide copolymers.

12. The implant according to claim 6 wherein the PLA copolymers are selected from the group consisting of lactide/tetramethylglycolide copolymers, lactide/trimethylene carbonate copolymers, lactide/d-valerolactone copolymers and lactide/ε-caprolactone copolymers.

13. The implant according to claim 6 wherein the PLA terpolymers are selected from the group consisting of lactide/glycolide/trimethylene carbonate terpolymers, lactide/glycolide/ε-caprolactone terpolymers, and PLA/polyethylene oxide copolymers.

14. The implant according to claim 1, wherein said resorption time is 5-30 months.

\* \* \* \* \*